United States Patent
Bixler et al.

(10) Patent No.: US 9,040,876 B2
(45) Date of Patent: May 26, 2015

(54) MULTI PURPOSE HEATING AND COOLING SAFETY DEVICE

(76) Inventors: Dick Bixler, Minneola, KS (US); Nancy Cudney Bixler, Minneola, KS (US)

( * ) Notice: Subject to any disclaimer, the term of this patent is extended or adjusted under 35 U.S.C. 154(b) by 790 days.

(21) Appl. No.: 13/151,773

(22) Filed: Jun. 2, 2011

(65) Prior Publication Data

US 2011/0297659 A1 Dec. 8, 2011

Related U.S. Application Data

(60) Provisional application No. 61/350,657, filed on Jun. 2, 2010.

(51) Int. Cl.
| | |
|---|---|
| *B60L 1/02* | (2006.01) |
| *H05B 1/00* | (2006.01) |
| *H05B 3/00* | (2006.01) |
| *H05B 3/34* | (2006.01) |
| *H05B 3/06* | (2006.01) |
| *B60H 1/00* | (2006.01) |
| *B60H 1/22* | (2006.01) |
| *F24H 3/04* | (2006.01) |
| *F24H 3/08* | (2006.01) |
| *A61G 7/057* | (2006.01) |
| *A61F 7/00* | (2006.01) |
| *A61F 7/08* | (2006.01) |
| *A61G 5/10* | (2006.01) |

(52) U.S. Cl.
CPC ............ *B60H 1/00564* (2013.01); *H05B 3/342* (2013.01); *B60H 1/2225* (2013.01); *B60H 2001/00235* (2013.01); *B60H 2001/229* (2013.01); *F24H 3/0429* (2013.01); *F24H 3/081* (2013.01); *A61G 7/057* (2013.01); *A61F 7/0053* (2013.01); *A61F 7/08* (2013.01); *A61F 2007/0071* (2013.01); *A61F 2007/0075* (2013.01); *A61F 2007/0084* (2013.01); *A61F 2007/0086* (2013.01); *A61F 2007/0094* (2013.01); *A61G 2005/1045* (2013.01); *A61G 2210/70* (2013.01); *A61G 2210/90* (2013.01)

(58) Field of Classification Search
CPC .... H05B 3/00; H05B 3/342; H05B 2203/036; H05B 3/50; H05B 2203/017; B60H 1/2225; B60H 1/00564; B60H 2001/00235; B60H 2001/229; F24D 13/024; F24H 3/0429; F24H 3/081; A61G 7/057; A61G 2005/1045; A61G 2210/70; A61G 2210/90; A61F 7/0053; A61F 7/08; A61F 2007/0071; A61F 2007/0075; A61F 2007/0084; A61F 2007/0086; A61F 2007/0094
USPC ......... 219/201–202, 211–213, 520, 528–529, 219/528–259
See application file for complete search history.

(56) References Cited

U.S. PATENT DOCUMENTS

| 2,504,308 | A | * | 4/1950 | Donkle, Jr. ...................... 62/261 |
| 2,991,627 | A | * | 7/1961 | Suits .............................. 62/3.5 |

(Continued)

FOREIGN PATENT DOCUMENTS

GB 2074803 * 11/1981 ............... H02H 5/04

*Primary Examiner* — Tu B Hoang
*Assistant Examiner* — Michael Hoang
(74) *Attorney, Agent, or Firm* — Fellers, Snider, Blankenship, Bailey & Tippens, P.C.; David G. Woodral

(57) ABSTRACT

A heating and cooling device is disclosed. The device has an outer covering, and a plurality of heating and cooling coils within the covering. A plurality of flexible air flow chambers inside the covering provide air flow over the heating and cooling coils, and a plurality of vents exit the outer covering from the plurality of air conduits.

13 Claims, 16 Drawing Sheets

(56) References Cited

U.S. PATENT DOCUMENTS 4,777,802 A * 10/1988 Feher ................................ 62/3.3
2006/0150331 A1 * 7/2006 Child et al. ........................ 5/502
2007/0256399 A1 * 11/2007 Yang ................................ 55/418

* cited by examiner

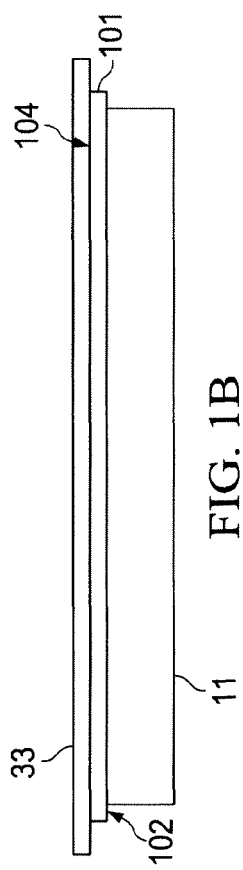

MULTI PURPOSE HEATING AND COOLING SAFETY DEVICE

CROSS REFERENCE TO RELATED APPLICATIONS

This application claims the priority of U.S. Provisional Patent Application No. 61/350,657 entitled "MULTI PURPOSE HEATING AND COOLING SAFETY DEVICE," filed Jun. 2, 2010, the contents of which are hereby incorporated by reference.

FIELD OF THE INVENTION

This disclosure relates to automobiles in general and, more specifically, to improving visibility through automotive glass.

BACKGROUND OF THE INVENTION

Snow and ice accumulation during drive presents a hazard faced by many motorists. It is frequently reported by motorists in accidents that the other driver was not seen approaching or that vision was somehow obscured by weather conditions, including snow or ice build-up on the vehicle windows. Modern vehicles are equipped with defrosters and climate control systems but these are based only on blowers near the lower half of the windshield. These may not keep ice off the upper half of the windshield—the area most critical for a driver to have a clear view—particularly under heavy ice or snow conditions.

What is needed is a system for addressing the above, and related, concerns.

SUMMARY OF THE INVENTION

The invention of the present disclosure, in one aspect thereof comprises a heating and cooling device. The device has an outer covering, and a plurality of heating and cooling coils within the covering. A plurality of flexible air flow chambers inside the covering provide air flow over the heating and cooling coils, and a plurality of vents exit the outer covering from the plurality of air conduits.

In one embodiment, the heating and cooling coils contain resistive heating elements. In other embodiments a first side of the covering provides a solid state heat transfer device to move heat out of the cooling coils to a heat sinking surface. The heating and cooling coils may be adapted to receive heating and cooling from an outside source.

The outer covering may define a rollable blanket. The heating and cooling device may also comprise a control and airflow box providing operating controls and air pressure into the air flow chamber. An air filtration system may be provided within the flexible air flow chambers.

In addition to other structures, the heating and cooling device may provide a plurality of resistive heating wires providing conductive heating through the surface of the covering The invention of the present disclosure, in another aspect thereof, comprises a method of heating and cooling. The method includes providing a covering blanket containing at least one flexible air path therein and at least one air vent for the air path exiting the covering blanket, providing heating and cooling coils in fluid communication with the flexible air path, and providing air under positive pressure into the flexible air path and selectively operating the heating and cooling vents to produce heated and cooled air, respectively, from the air vent.

The method may also include placing the covering blanket on the interior roof of a vehicle to climate control the vehicle and provide window defrosting, and/or connecting the covering blanket to a heating, ventilation, and air conditioning system of an automobile for providing air pressure into the flexible air path. Coolant may be provided into the cooling coils from an automobile mounted compressor.

In some embodiments the method includes providing the covering blanket as a part of a bedding surface, or providing the covering blanket as part of a seating surface.

BRIEF DESCRIPTION OF THE DRAWINGS

FIG. 1B is a side cutaway view of a portion of the vehicle roof of FIG. 1A.

DETAILED DESCRIPTION OF THE PREFERRED EMBODIMENTS

The system of the present disclosure is designed to assist in lowering traffic deaths and wrecks due to ice and snow build-up on vehicles windows, particularly while driving. The system of the present disclosure will assist in providing clear vision for the driver via heating and cooling from the top of the windshield (nearer to the driver's eye level). A stand-alone version is disclosed to adapt to older vehicles. An integrated version may be built into new vehicles. In one embodiment, the device is a blanket that may be built into or between the headliner and roof and connected to the heating and cooling system. The device may be adapted to or built into a new vehicle using the vehicle power supply. In some embodiments, the device may be partially or fully solar or battery powered.

In alternative embodiments, the device is multi-purpose and transformative in that the combined components and different shapes can be adapted to implements such as hospital bed, wheelchair, camping stadium seat, and other devices. Uses of the device may include safety considerations, such as keeping ice off vehicle windows and treating or preventing hypothermia, but may also include comfort uses such as warming and cooling stadium seats, or the wheelchair bound. In one embodiment, the device may be utilized as a heating and cooling blanket or pad on the ground while camping. The device may also be useful in veterinary medicine.

The automotive embodiments of the device of the present disclosure can be adapted to start by remote, or a timer, to heat or cool the vehicle and/or defrost windows before a person gets into the vehicle. The device may be powered via an auxiliary battery, may be solar powered, or powered from the vehicle electrical system. In one embodiment, the device is self-contained and provides all controls, such as heating and cooling controls, fan speed, thermostat, safety shut off, and on/off switches. Controls may also be built into the vehicle's dashboard or similar location, and/or use a remote control system—particularly where the device is integrated into the vehicle.

The apparatus of the present disclosure has multiple embodiments that may provide thermostats, shut-offs, solar battery storage, heat/cooling shields, heating and cooling thermal wiring, conversion embodiments, monitor controls, timer safety components, and more. The apparatus blanket is multipurpose (being self contained) and can work in a vehicle or as a heating and cooling ventilation system to assist people in staying warm or cool in remote areas.

Figure 1A:
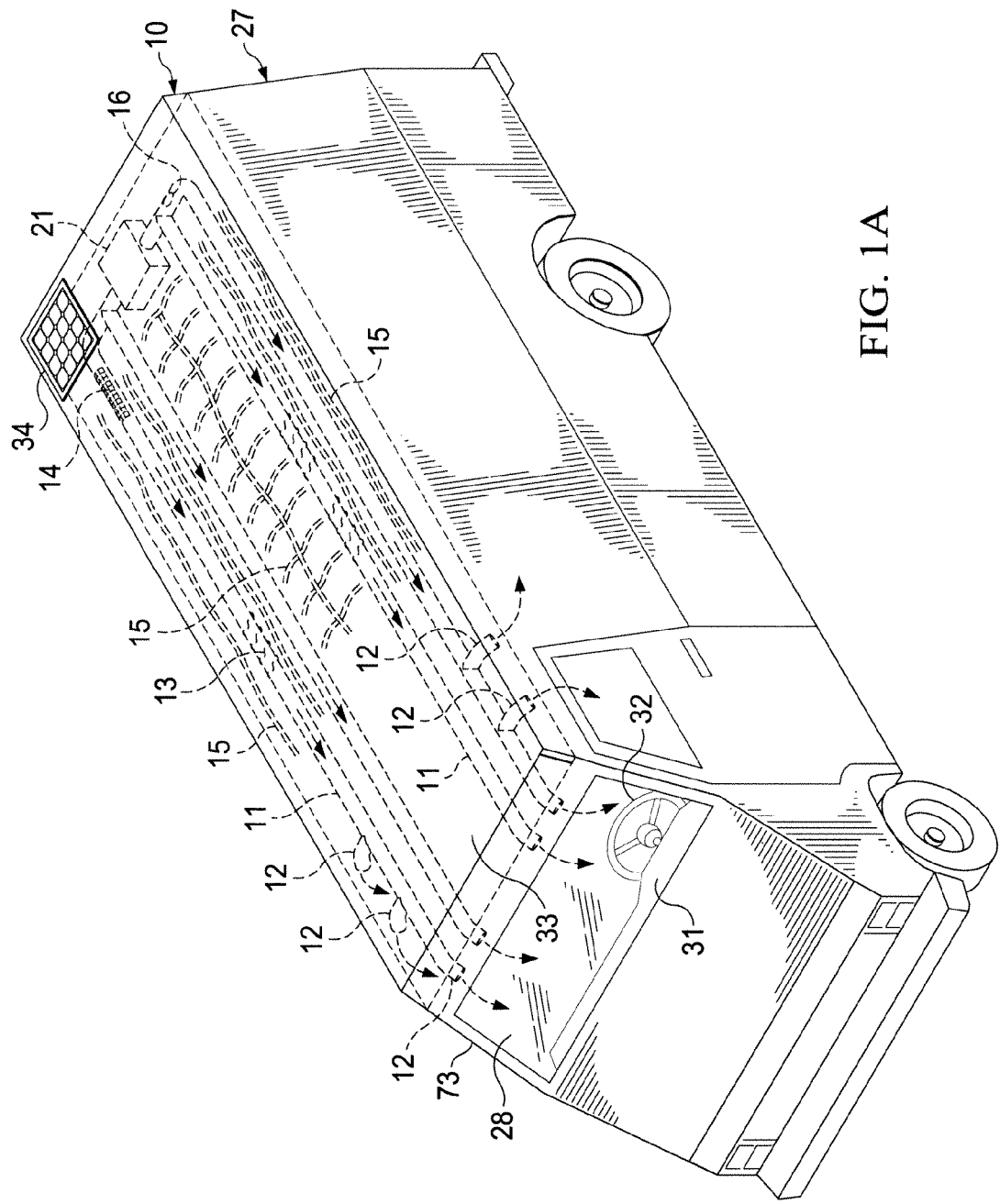
FIG. 1A is a perspective view of the heating and cooling device of the present disclosure installed in a vehicle.

Referring now to FIG. 1A, a top view of a heating and cooling device 100 of the present disclosure is shown. The device 100 (shown in broken line) is situated between a new vehicle roof top and the inside headliner. In the present embodiment, the device 100 has a housing 10, which lies under the vehicle rooftop 33, and is surrounded by the vehicle body 27. The body 27 is part of the vehicle frame tube 73. A vehicle windshield 28 is attached to the body 27 and/or frame 73. A vehicle dashboard 31 and vehicle steering wheel 32 are illustrated as well.

Flexible air flow chambers 11 are shown attached to a female control box housing 21. The control box houses multi-operational and functional components assisting in operating and controlling the apparatus. The housing 10 also contains heating and cooling blanket wires 15, which serve to heat or cool the blanket surface. Thus, in some embodiments, the blanket may provide conductive heating or cooling by conduction against another surface or to a user.

The flexible air flow chamber 11 houses a fiber filter system 14. This allows for filtration of the air from the control box 21. It is understood that each air flow chamber 11 may have its own filtration system. The filtration systems may guard against bacterial and/or particulate contamination. In another embodiment, the control box 21 will provide filtration for the entire system. Heating and cooling sensors 16 may provide temperature readings to the control box 21. The air flow chamber 11 provides air flow outlet tubes 12 embraced by heating and cooling coils 13. Heating and cooling coils 13 serve to either heat or cool the air flowing from the outlet tubes 12.

In some embodiments, a solar panel 34 (shown implanted to the vehicle roof top 33, FIGS. 1A, 4) may provide some or all the power to run the device 10.

It will be appreciated that heating may be done resistively within the device of the present disclosure (e.g., by coils 13 and/or wires 15). However, providing cooling in addition to that based solely on increased convection from moving air presents unique challenges. In some embodiments, the device 10 will rely on refrigerated air from the air condition system of the host vehicle. In other embodiments, a separate compressor and cooling system may be provided (where enough power can safely be provided to do so). Finally, a solid state solution such as a peltier cooler 101 could be provided (see FIG. 1B). These could be arranged with the cold side 102 on the air ducts 11 and the hot side 104 toward the roof of the automobile; thus using the roof of the car 33 as a heat sink that can be cooled by the outside air, possibly leading to increased efficiency.

Figure 2:
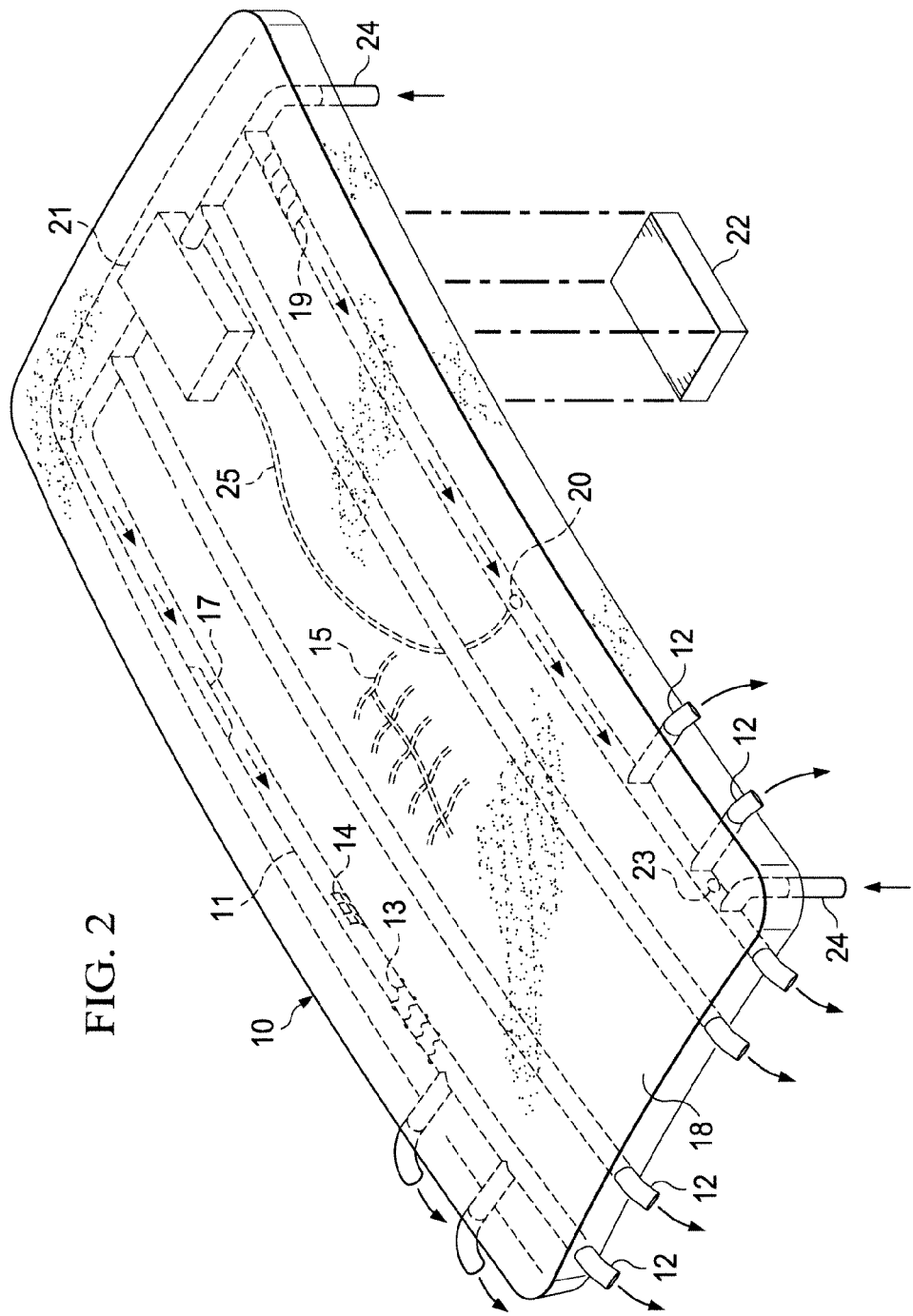
FIG. 2 is a perspective view of the device of FIG. 1 showing additional internal componentry.

Referring now to FIG. 2, a top perspective view of the blanket 10 is shown. Here, two portions of the control box are shown: a female control box housing 21 combined with a male control box housing 22. These provide a housing for the fan, as well as various relays, switches, and other control components. Various control devices may also be provided away from the housing 22. For example, a control valve 23 may activate or deactivate various vents 12 and/or airflow chambers 11. Additionally, supplemental air intakes 24 may be provided to allow the device 10 to work in conjunction with the system built into the automobile. In some embodiments, one or more booster fans 20 may be provided within chambers 11, supplied with power by supplemental wiring 25.

The chambers 11 may be provided with insulation 17 over all or a portion thereof. The air flow chambers 11 are provided with the filtration system 14, and the heating and cooling coils 13. At the ends of chambers 11 are directional detachable air flow outlet tubes 12. Supplemental insulation 19 may also be provided where needed.

The outer layer of the device 10 may be an insulated blanket-like cover 18. The material comprising the cover may vary according to its intended use. In some embodiments, materials will be selected to match the interior of a vehicle. In other embodiments, materials may be selected with user comfort in mind. Finally, aesthetics may be considered and the covering 18 could be decorated with various designs, such as those of a sports team.

Figure 3:
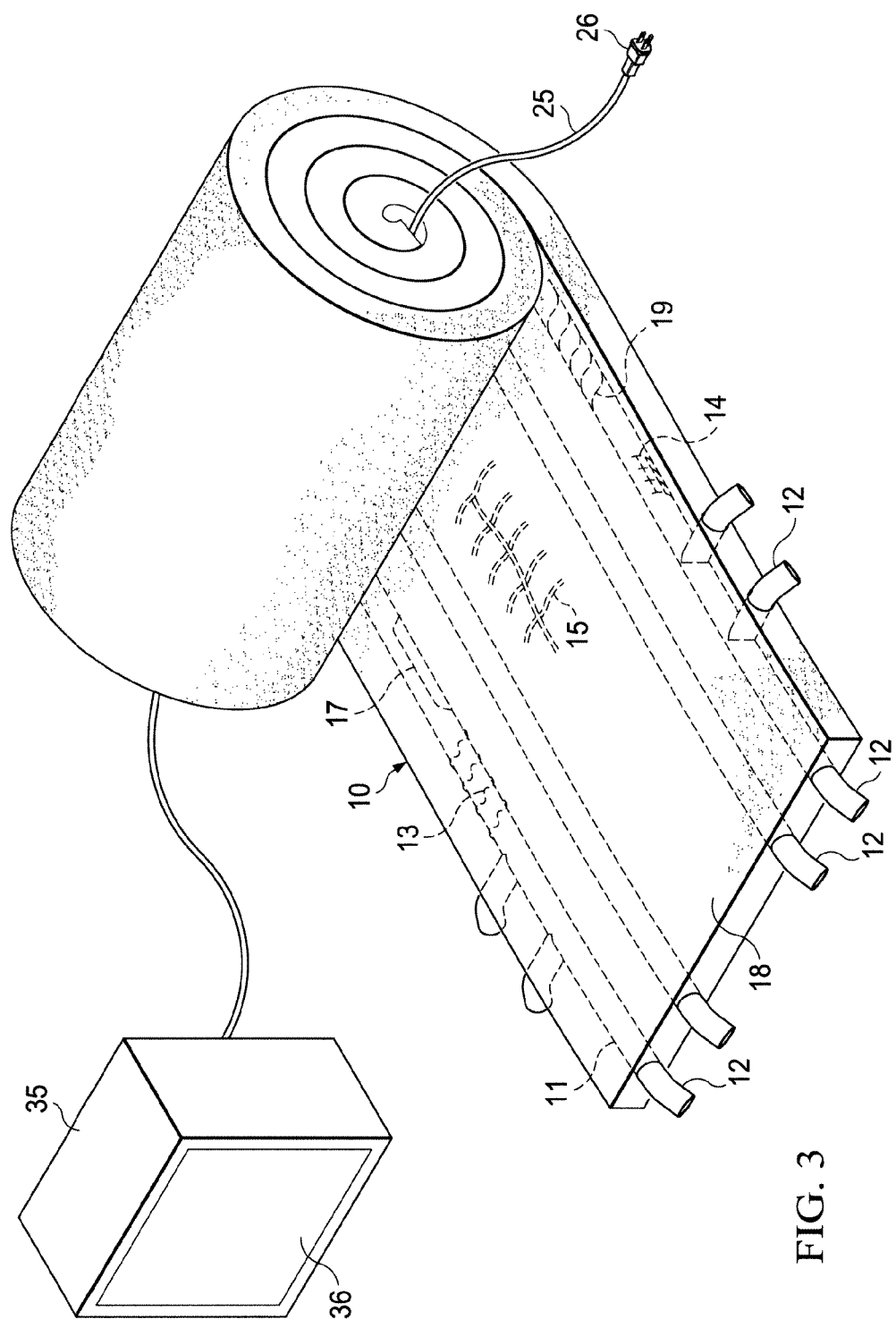
FIG. 3 is a perspective view of a heating and cooling device of the present disclosure partially rolled up.
Figure 7:
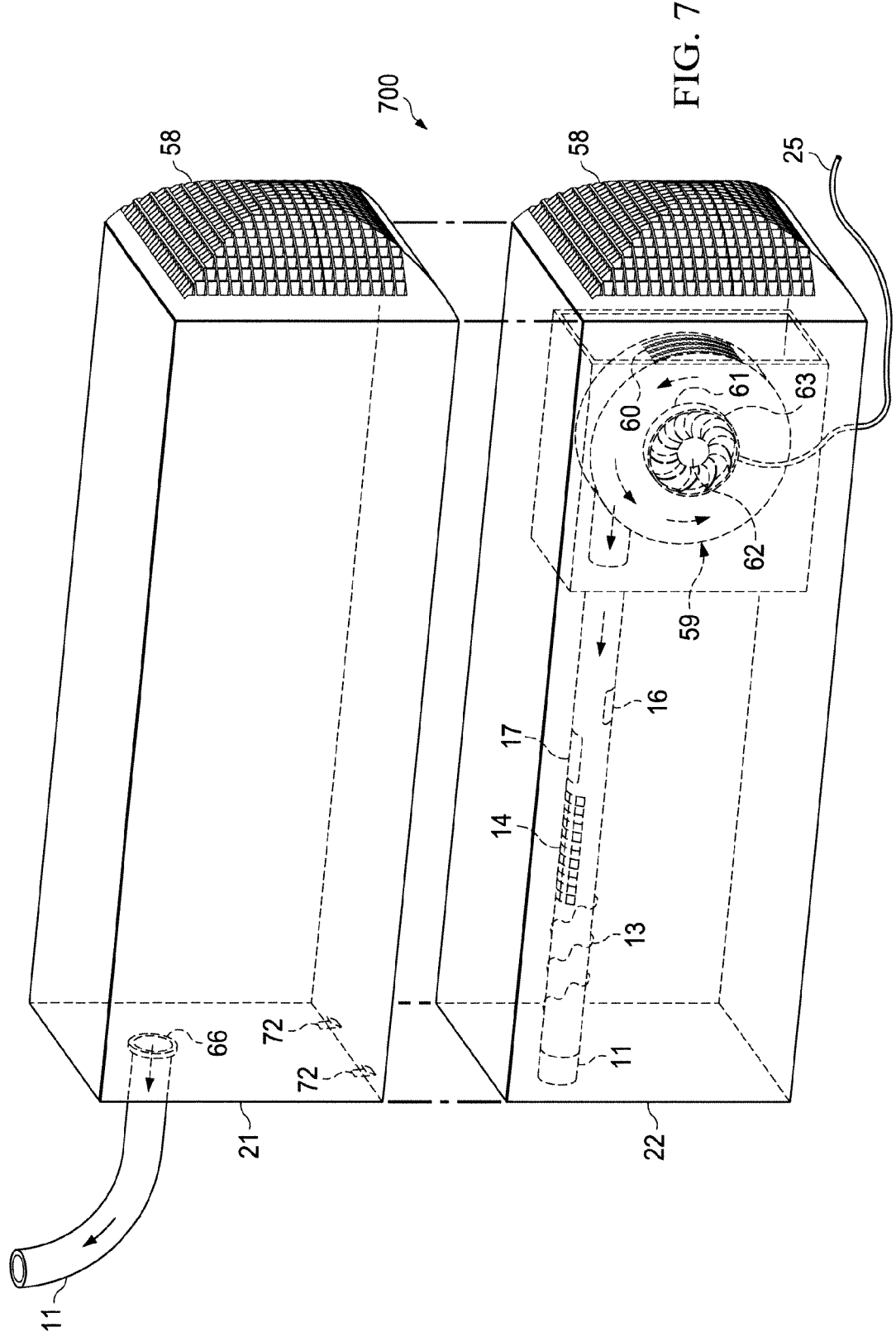
FIG. 7 is another perspective view of another control box according to the present disclosure.

Referring now to FIG. 3, a perspective view of a heating and cooling device 10 of the present disclosure partially rolled up is shown. Here the flexibility of the device 10 can be seen. The directional detachable air flow outlet tube 12 and insulated cover 18 can also be seen. The power supply wiring 25 is connected to a standard plug 26. A manually controlled housing 35 contains blowers, switch gear, and the like. An access door panel 36 may also be provided. The device 10 may also be connected another external air supplies device 700, such as shown in FIG. 7 below.

Figure 4:
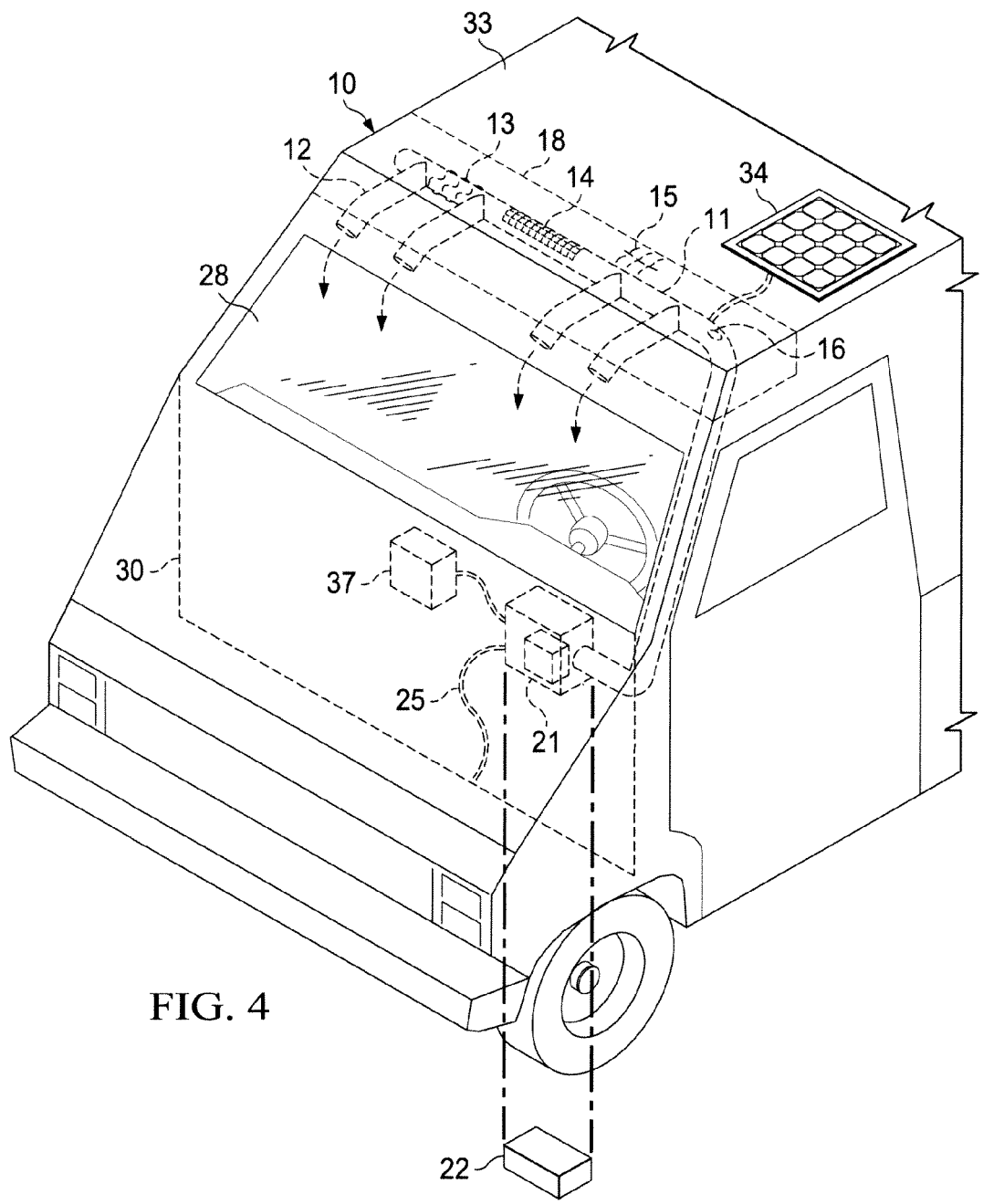
FIG. 4 is a perspective cutaway view of the front of a vehicle integrated with a heating and cooling device of the present disclosure

Referring to FIG. 4, a perspective cutaway view of the front of a vehicle integrated with a heating and cooling device 10 of the present disclosure is shown. The device 10 is installed to provide heating and cooling, as well as defrosting for windshield 28. Control panel housing 37 is affixed to vehicle fire wall panel 30. Female control box housing 21 houses the male control box housing 22 when assembled, and further attaches to the fire wall 30. Shown in front of the vehicle firewall panel 30 is the power supply wiring 25. Attached to housing 21 is flexible air flow chamber 11. Above and behind windshield 28 are the directional detachable air flow tubes 12. Chamber 11 houses heating and cooling coils 13, and filter system 14. A temperature sensor 16 is also provided. FIG. 4 also shows the vehicle roof top 33 with a solar panel 34 attached to or embedded in roof 33.

Figure 5:
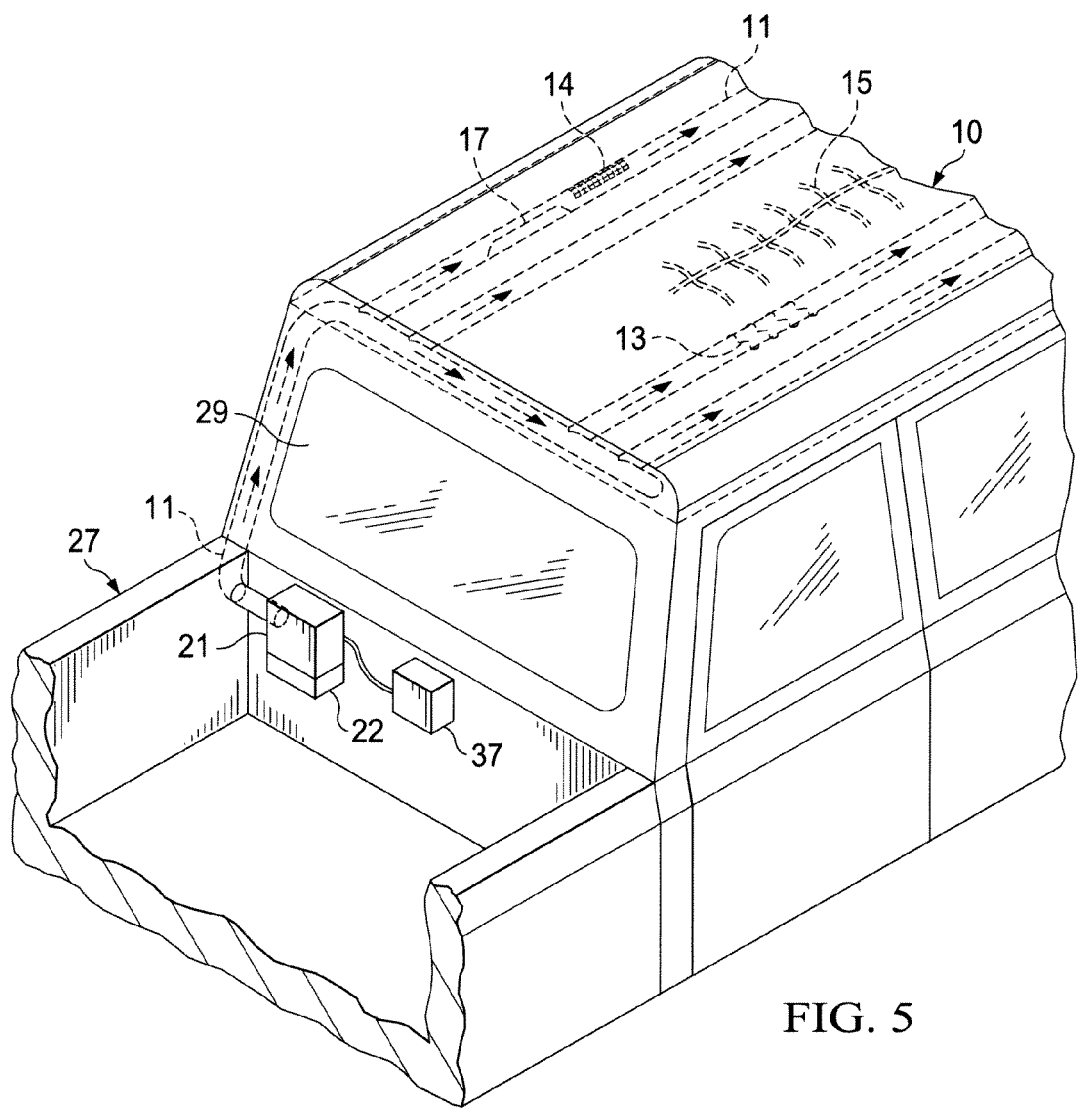
FIG. 5 is a rear perspective view of another vehicle with an integrated heating and cooling device.

Referring now to FIG. 5, a rear perspective view of another vehicle with integrated heating and cooling device 10 is shown. A vehicle body 27 supports the female control box housing 21 and male control box housing 22, shown here locked together. Flexible air flow chamber 11 connects to housings 21, 22 and to existing heat and air conditioner units in a vehicle. The solar power conversion housing 37 can be seen here, as can heat and cool (thermal) shield 17 and filter system 14. Heating and cooling coils 13 are shown as part of chamber 11, and heating and cooling blanket wiring 15 is also provided. A standalone air supply device 700 such as shown in FIG. 7 could also be provided and attached to the device 10 shown in FIG. 5.

Figure 6:
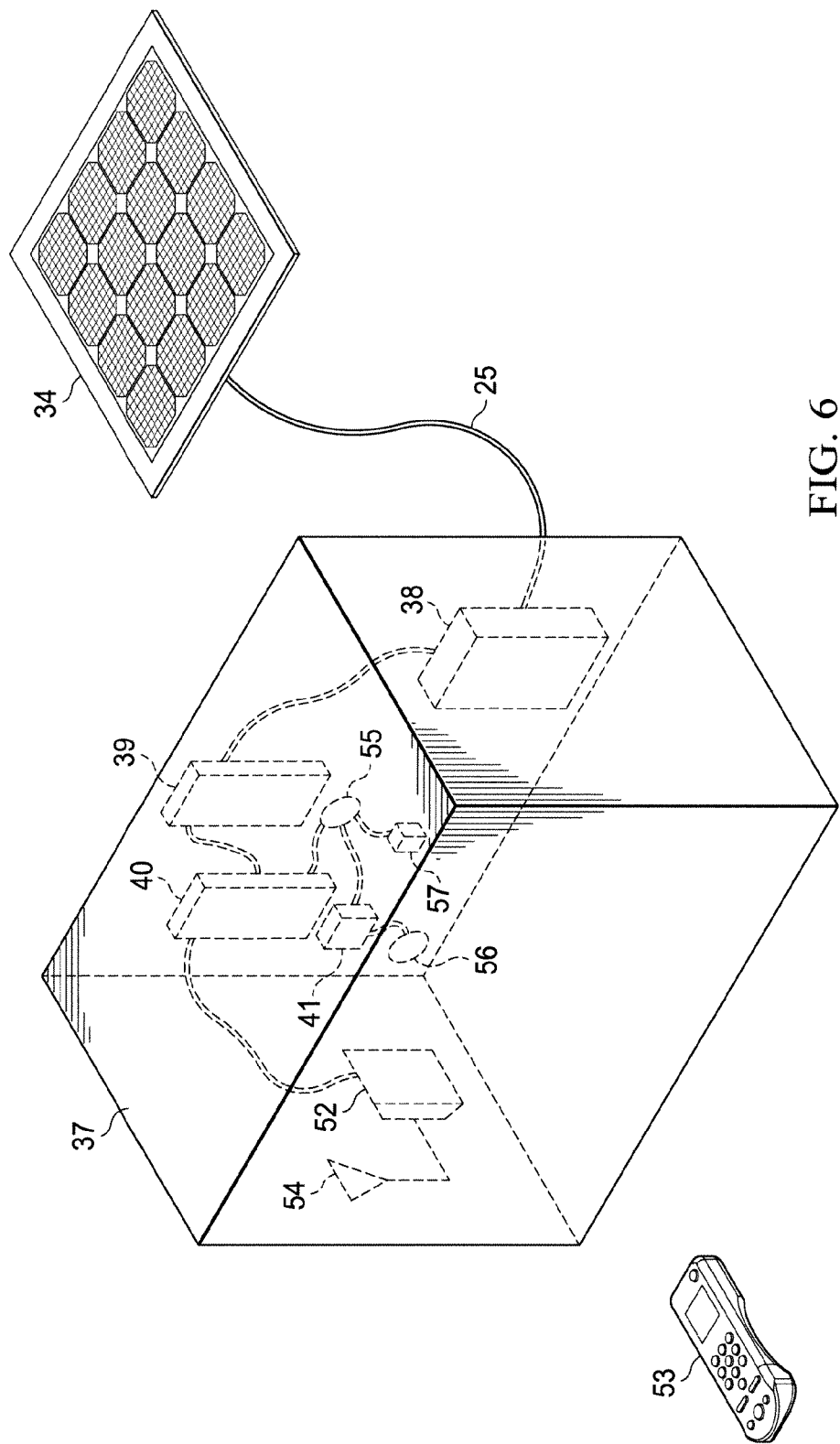
FIG. 6 is a perspective view of a control box according to the present disclosure.

Referring now to FIG. 6, a perspective view of a control box according to the present disclosure is shown. A housing 37 houses a separate monitor and control unit 40. This may be based on a solid state microcontroller in combination with various switchgear, relays, and the like. Battery power storage 39 is provided, along with a solar converter 38, which provides for voltage regulation from the solar panel 34. A thermostat monitor control unit 55, a fuse box housing 57, and a thermostat 56 are provided in the present embodiment. An override control unit 41 may be provided for manual operation of the entire system. In the present embodiment, an antenna 54 and a remote control master unit 52 allow for remote operation of the device from the remote control 53.

Referring now to FIG. 7, another perspective view of another control box according to the present disclosure is shown. This box 700 provides on example of a standalone unit capable of providing air flow and/or heating and cooling. The female control box housing 21 is shown above the male control box housing 22. An attachment locking system 72 is provided for securing the halves together. This may comprise clamps or other captive fasteners. In the present embodiment, housing 59 houses a motor housing 61, which secures a drive motor 62. Drive motor 62 operates a fan 63 to pull in air through safety vent screens 60 and 58. Air is moved through the flexible air flow chamber 11, through filter system 14 and the heating and cooling coils 13. Safety shield 17 may be provided as well as the temperature sensor 16. Power may be supplied through the power supply wiring 25, which may be connected to the vehicle electrical supply, a solar power supply, or other power source.

Figure 8:
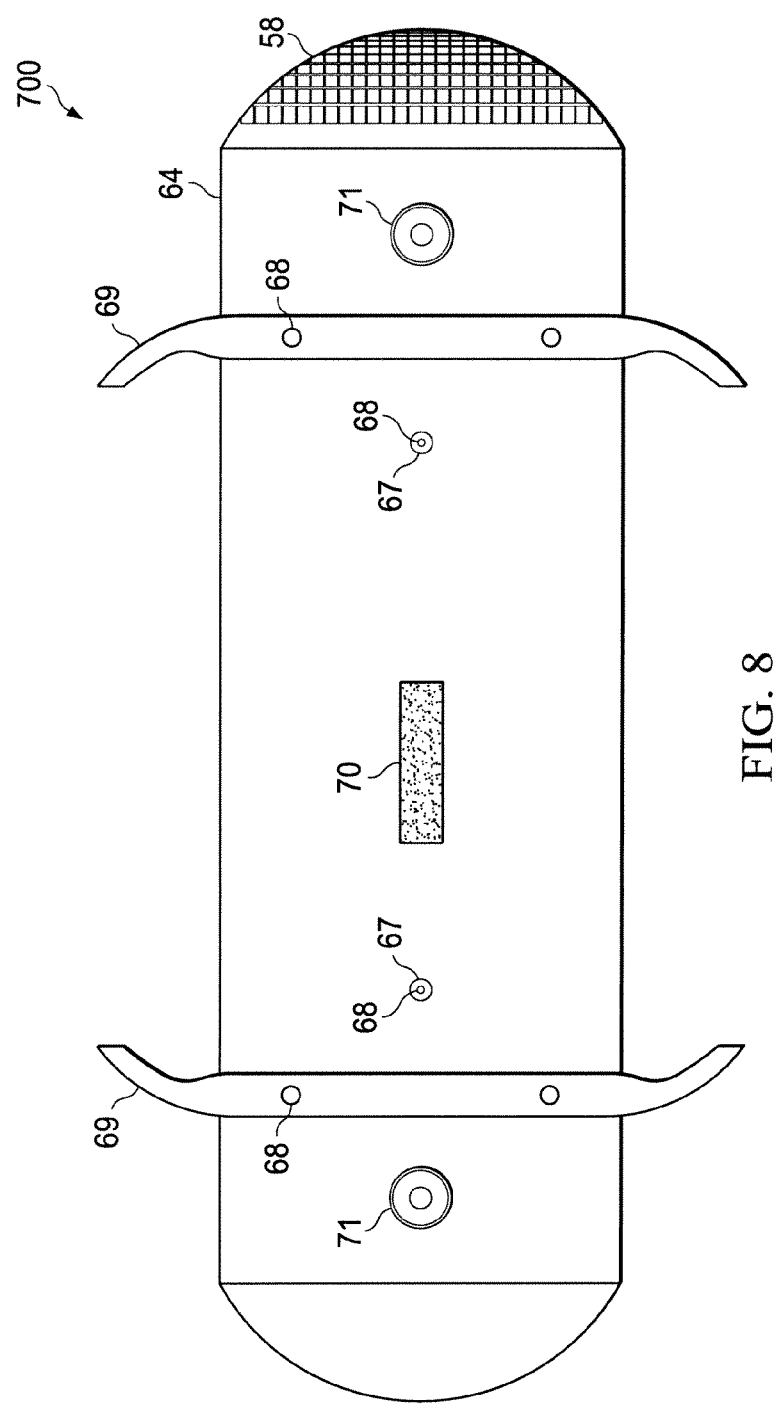
FIG. 8 is a top view of another control box to be retrofitted to an older vehicle.

Referring now to FIG. 8, a top view of another control box to be retrofitted to an older vehicle is shown. FIG. 8 may be considered a top down view of FIG. 7. This version may be secured to a vehicle or other fixture. Attachment clamp system 69 is provided to secure the housing 64. Clamps 69 may be attached by rivets or bolts 68 to the housing 64. In other embodiments, other securement means may be provided including a suction cup system 71, Velcro® strips 70, or other temporary or permanent fasteners. A penetrating locking device receptacle 67 may be provided as a secure attachment point for the housing 64.

Figure 9:
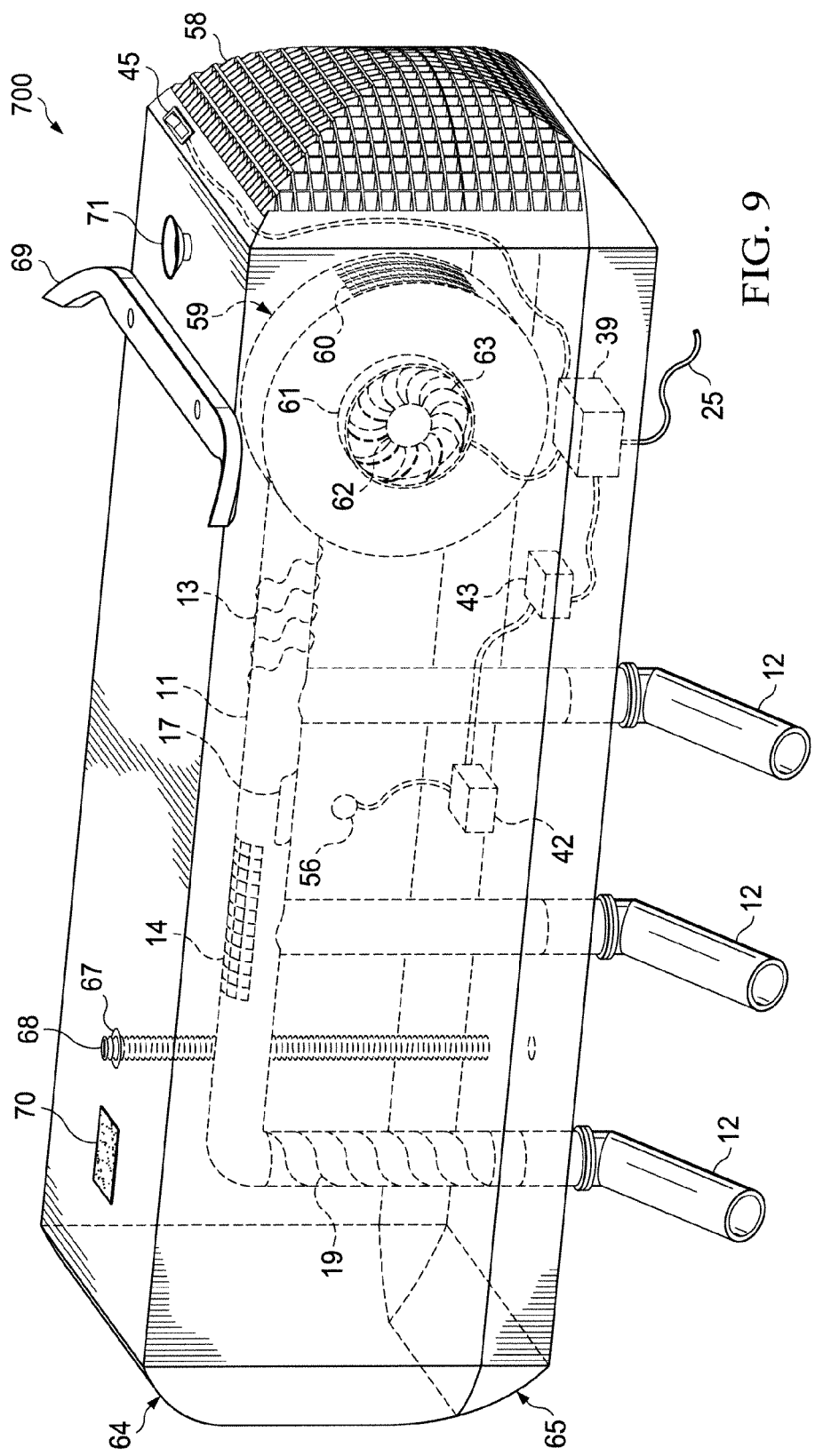
FIG. 9 is a perspective view of a control box to be retrofitted to an older vehicle according to aspects of the present disclosure.

Referring now to FIG. 9, a perspective view of a control box to be retrofitted to an older vehicle according to aspects of the present disclosure is shown. FIG. 9 illustrates the device of FIGS. 7-8 with greater internal detail. Here, an auxiliary on/off switch 45, air inlet vent and screens 58 are illustrated. A penetrating locking device comprising a long bolt 68 is shown within the receptacle 67. This will secure the apparatus 10 to a fixed structure. Upper housing 64 is shown attached to lower housing 65.

Placed inside housing components 64, 65 are various multipurpose functional and mechanical implements. These may include, but are not limited to, the air intake/exit housing 59, having an inlet which has a safety vent screen 60 allowing air to be sucked through by the motor 62 which is inside the motor housing 61. The motor 62 may be attached to the fan system 63. Fan system 63 circulates into and out of housing 59, into the flexible air flow chamber 11, and exiting out the directional database air flow outlet tubes 12. Inside and around chamber 11 are the heating and cooling coils 13, the heat and cool shields 17, the fiber filter system 14, and the heat and cool air insulated wrap 19.

In some embodiments, a thermostat 56 may be provided. Control housing 42 is shown connected to automatic shut off control 43. A battery pack 39 is integrated with the power supply wiring 25 for recharging.

Figure 10:
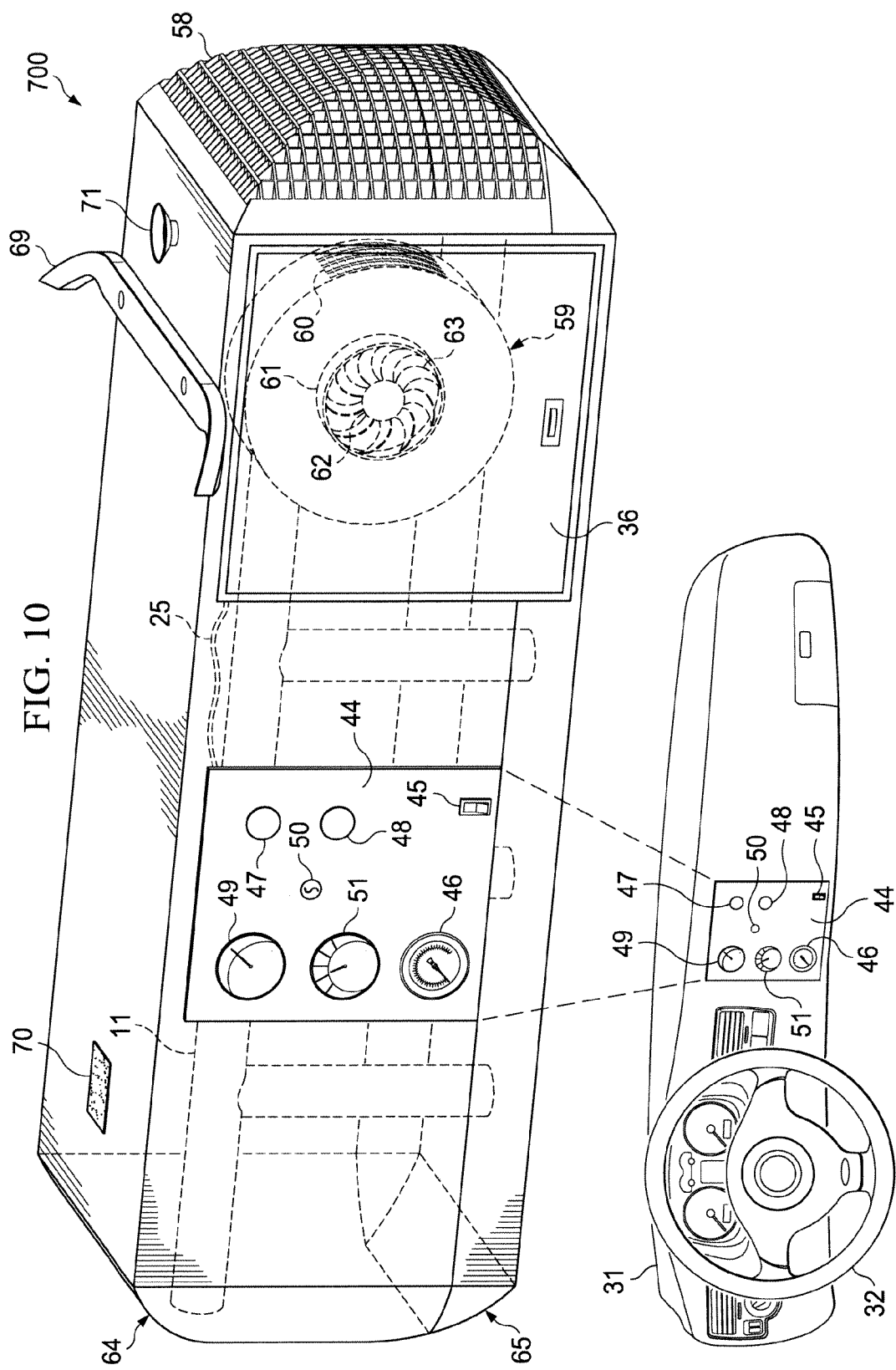
FIG. 10 is a view of a control box integrated with a vehicle dashboard.

Referring now to FIG. 10, a view of a control box integrated with a vehicle dashboard, and a front view of the apparatus is shown. Attached to the apparatus 10 is a control panel 44 which may contain various switch gear and controls. In the present example, these include an auxiliary on/off switch 45, an on light 48, an off light 47, an auxiliary solar power switch 50, a fan speed control 51, an automatic/manual timer 46, and a heat and cool control 49. These may be variously powered by power supply wiring 25.

The lower illustration in FIG. 10 shows that the apparatus can be installed across multiple places. Here, the control panel is placed a vehicle dashboard 31. The control panel 44 may be a part of the factory installed controls of the vehicle, or may be added when the apparatus 10 is installed.

Figure 11:
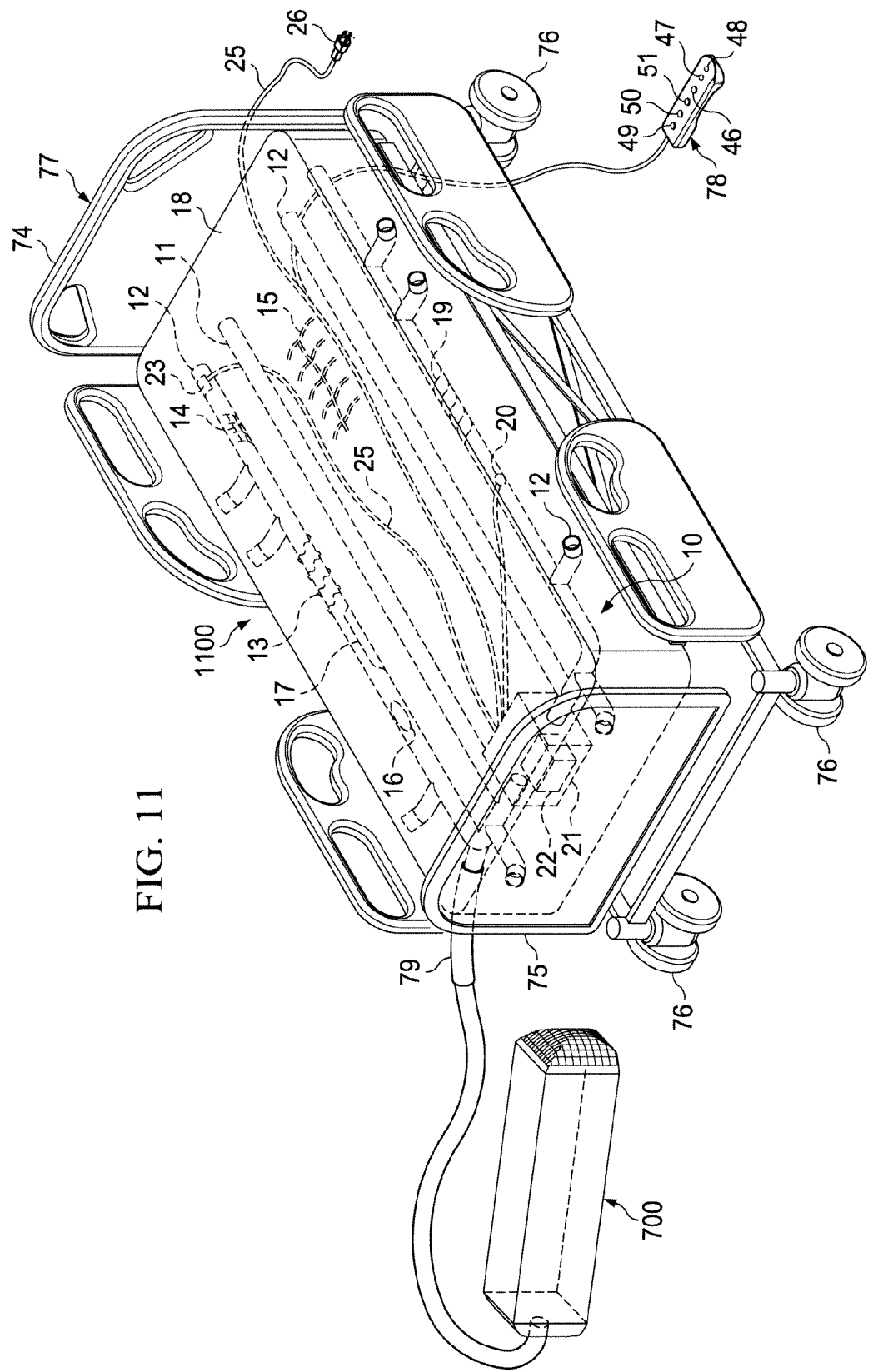
FIG. 11 is a perspective view of a heating and cooling device according to the present disclosure having been integrated into a hospital bed.

Referring now to FIG. 11, a perspective view of a heating and cooling device 1100 according to the present disclosure having been integrated into a hospital bed is shown. A headboard 74, footboard 75, and wheels 76 are shown on bed 77. As before, cooled air could be provided by a building-installed HVAC system or a smaller dedicated system. An adapter 79 allows the device 10 to be connected to a standalone unit 700, or connected to the hospital HVAC system. Standalone unit 700 may be used instead of an integrated one to control noise. Female control box housing 21 attaches to the male control box housing 22, forming a complete housing for components including, but not limited to, those shown and discussed previously. FIG. 11 also shows the flexible air flow chambers 11 housing the heat and cool sensors 16, switch control valve door 23, and booster air flow fan 21. Other inlets and connections may also be provided to the device 100 including a filtered air inlet and/or an oxygen inlet (not shown). Such connections may be capped off when not in use.

Figure 12:
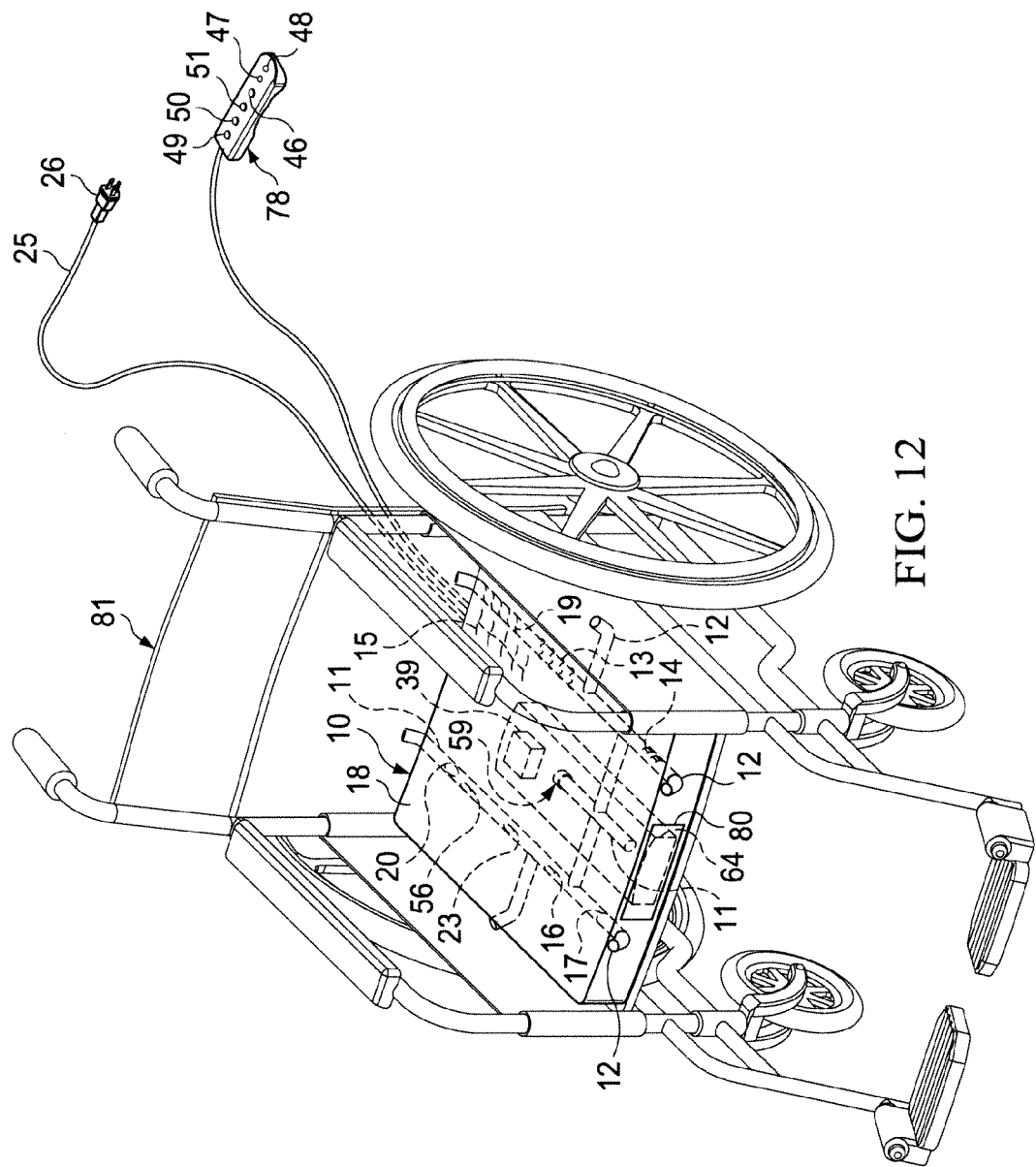
FIG. 12 is a perspective view of a heating and cooling device according to the present disclosure having been integrated into a wheelchair.

Referring to FIG. 12, a perspective view of a heating and cooling device according to the present disclosure having been integrated into a wheel chair is shown. In the present embodiment, the device 10 houses a blanket access door 80 providing access to the upper housing 64. A battery pack 39 is provided for power. In some cases, an on board compressor may be needed to provide cool air to the blanket. In some cases, peltier cooling/heating may be employed. Heating may also be accomplished resistively.

Figure 13:
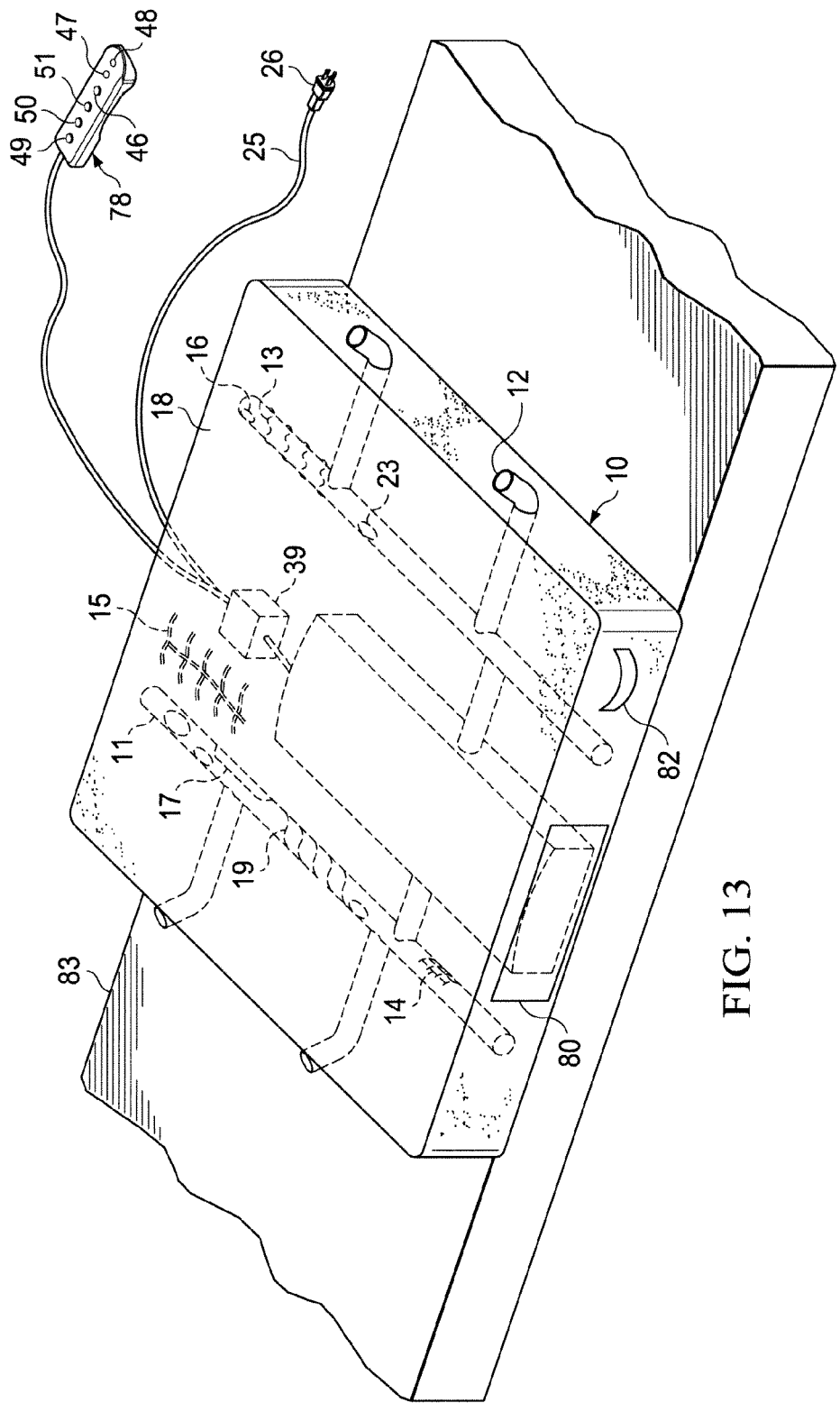
FIG. 13 is a perspective view of a heating and cooling device according to the present disclosure having been integrated into a stadium seat.

Referring now to FIG. 13, a perspective view of a heating and cooling device according to the present disclosure having been integrated into a stadium seat is shown. Here, the device 10 is similar to that shown in FIG. 12 and may be placed on a bleacher seat 83.

Figure 14:
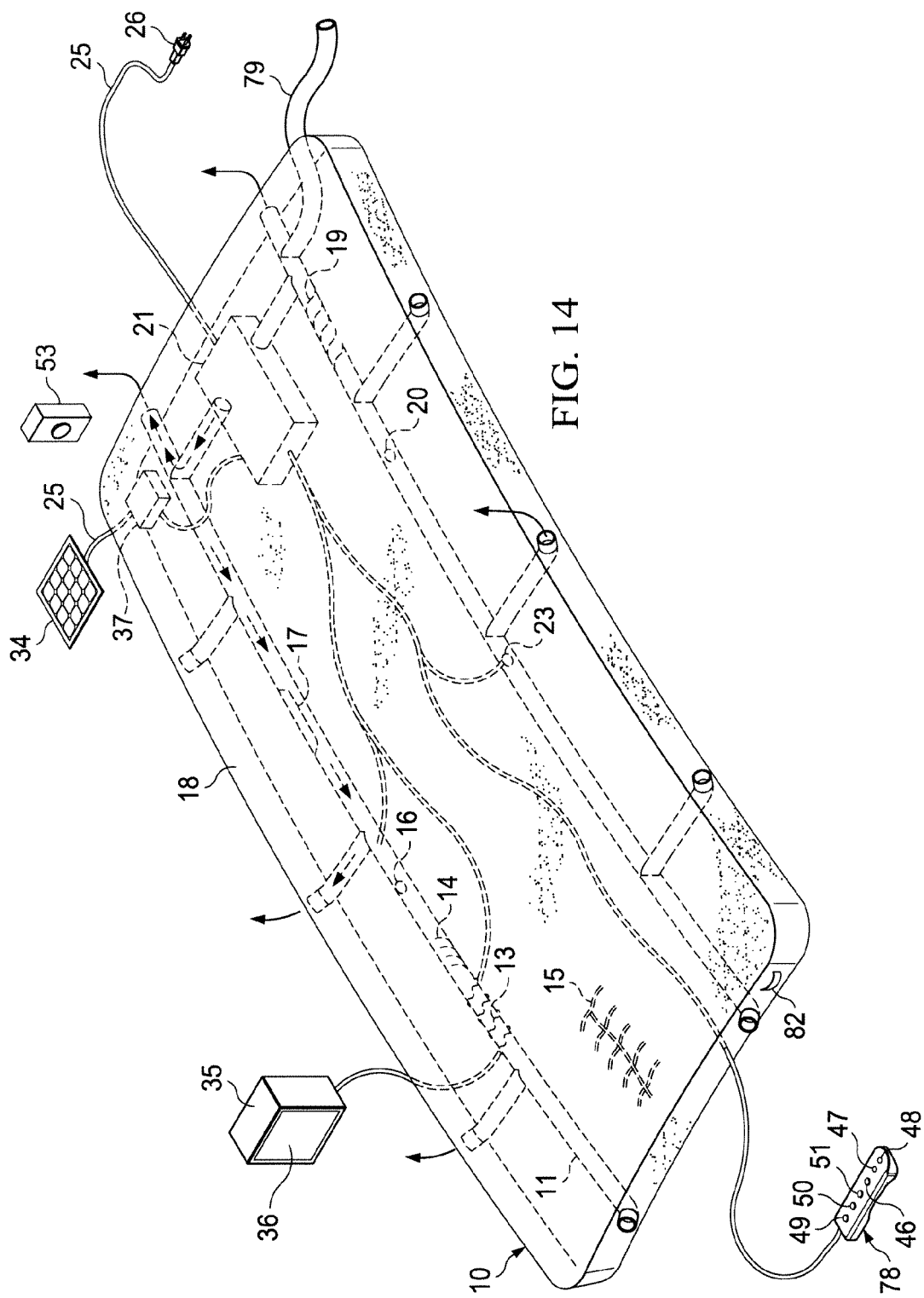
FIG. 14 is a perspective view of a heating and cooling device according to the present disclosure having been integrated into a sleeping mat.

Referring now to FIG. 14, a perspective view of a heating and cooling device according to the present disclosure having been integrated into a sleeping mat is shown. The device 10 may be used for camping to enhance comfort on hot or cold nights. It may also be used for treatment of hypothermia. Medical uses may also include cooling of the body when hypothermia is induced.

Figure 15:
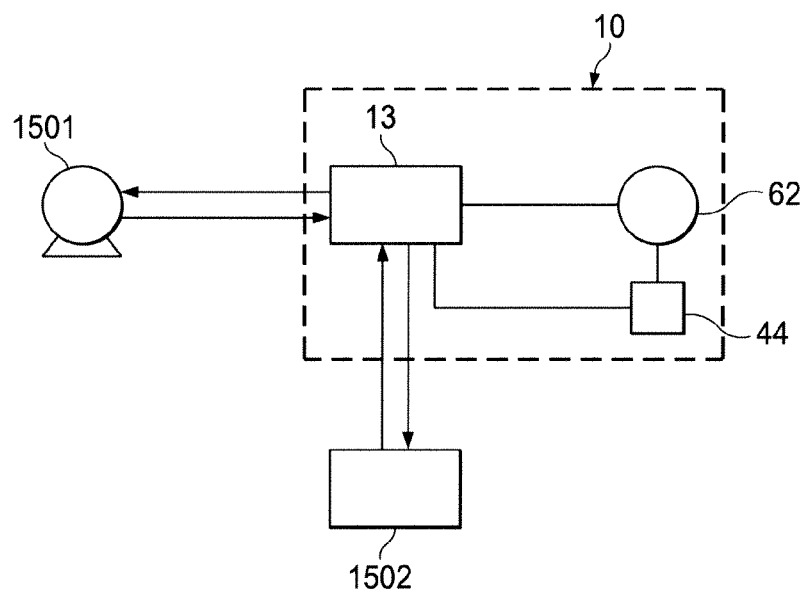
FIG. 15 is a block diagram illustrating a heating and cooling device attached to an outside heating and cooling source.

Referring now to FIG. 15, a block diagram illustrating a heating and cooling device attached to an outside heating and cooling source is shown. Here, cooling device 1501 provides refrigeration of a coolant. The coolant could be Freon, R134A, chlorine, water, or another suitable liquid of gas. It could be chilled by a compressor, condenser, and evaporator arrangement or by other means known in the art. The cooling device 1501 could be an automobile air conditioner system, a part of a commercial or residential building cooling system or a separate dedicated system. As shown, the refrigerated liquid may be provided to coils 13. The coils 13 are a part of the device 10 previously described. The coils 13 exchange heat (e.g., into an automobile, or with a user) and the now heated refrigerant is returned to the cooling device 1501 to be exchanged for more and colder coolant. Some, but not all, of the other components of the device 10 that may be included with various embodiments are shown for illustration. These include the blower 62 and control panel 44.

A heating device 1502 may also connect to the coils 13. The heating device 1502 could be an automotive heater core, a standalone water heater, or another device. Heated fluids are provided to the coils 13, which will be cooled by heat exchange with the automobile or user. The cooled fluid is then returned in exchange for more heated fluid. The heating fluid does not have to be water, nor even a liquid. For example, it could be heated oil. In another embodiment, the cooling device 1501 and the heating device 1502 are the same device and operate as a heat pump. In this way, the same fluid is used for both heating and cooling depending upon the state in which it is provided by the device.

While the invention has been described with a certain degree of particularity, it is manifest that many changes may be made in the details of construction, components, and the arrangements of components without departing from the spirit and scope of the disclosure. Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

What is claimed is:

1. A heating and cooling device comprising:
    an outer covering;
    a plurality of flexible air flow ducts inside the outer covering providing air flow from a fan to a plurality of vents on ends of the flexible air flow ducts; and
    a plurality of heating and cooling coils arranged within the outer covering on the flexible air flow ducts to provide heating and cooling to air flowing within the plurality of flexible air flow ducts;
    wherein the plurality of vents are affixed at predetermined locations on the outer covering providing for the air flow to exit the outer covering from the plurality of air flow ducts; and
    wherein the flexible air flow ducts prevent air from the fan from exiting the outer covering except through the plurality of vents, and from blowing through the outer covering except through the flexible air flow ducts.

2. The heating and cooling device of claim 1, wherein the outer covering defines a rollable blanket.

3. The heating and cooling device of claim 1, wherein the heating and cooling coils contain electrically resistive heating coils.

4. The heating and cooling device of claim 1, wherein a first side of the covering provides a Peltier cooler to move heat out of the cooling coils to a heat sinking surface.

5. The heating and cooling device of claim 1, wherein the heating and cooling coils are adapted to receive heating and cooling power from an outside source.

6. The heating and cooling device of claim 1, further comprising a control and air flow box providing operating controls and air pressure into the air flow ducts.

7. The heating and cooling device of claim 1, further comprising an air filtration system within the flexible air flow ducts.

8. The heating and cooling device of claim 1, further comprising a plurality of resistive heating wires providing conductive heating through the surface of the covering.

9. A heating and cooling system comprising:
    a flexible air flow duct in fluid communication at a first location with a control and air supply box and having an outlet vent at a second location;
    a heating coil on the flexible air flow duct and in fluid communication with the flexible air flow duct such that the heating coil heats air flowing through the flexible air flow duct; and
    a covering blanket containing the flexible air flow duct and the heating coil and having a predetermined location that passes the outlet vent therethrough;
    wherein the control and air supply box provides air flow under positive pressure into the flexible air flow duct and selectively activates the heating coil to provide heated air at the outlet vent; and
    wherein the flexible air flow duct prevents air from entering a space between the flexible air flow duct and the covering blanket from the flexible air flow duct.

10. The heating and cooling system of claim 9, wherein the heating coil also accepts coolant and operates as a cooling coil.

11. The heating and cooling system of claim 9, further comprising a Peltier cooler in fluid communication with the flexible air flow duct.

12. The heating and cooling system of claim 9, further comprising heating wires selectively providing resistive heating to the covering blanket.

13. The heating and cooling system of claim 9, wherein the flexible air flow duct has an air filter.

* * * * *